United States Patent [19]

Morgan

[11] 4,112,233
[45] Sep. 5, 1978

[54] HYDANTOIN-CONTAINING POLYENE COMPOSITIONS

[75] Inventor: Charles R. Morgan, Brookeville, Md.

[73] Assignee: W. R. Grace & Co., New York, N.Y.

[21] Appl. No.: 737,309

[22] Filed: Nov. 1, 1976

Related U.S. Application Data

[60] Continuation-in-part of Ser. No. 614,577, Sep. 18, 1975, abandoned, which is a division of Ser. No. 461,207, Apr. 15, 1974, Pat. No. 3,945,982.

[51] Int. Cl.² ............................................. C07D 233/72
[52] U.S. Cl. .................................................... 548/312
[58] Field of Search ........................ 260/309.5; 548/312

[56] References Cited

U.S. PATENT DOCUMENTS

| 3,839,354 | 10/1974 | Habermeier et al. | 260/309.5 |
| 3,852,302 | 12/1974 | Habermeier et al. | 260/309.5 |
| 3,864,357 | 2/1975 | Porret et al. | 260/309.5 |
| 3,867,385 | 2/1975 | Habermeier et al. | 260/309.5 |
| 3,886,123 | 5/1975 | Habermeier et al. | 260/309.5 |
| 3,893,979 | 7/1975 | Wolf et al. | 260/309.5 |
| 3,928,298 | 12/1975 | Wolf et al. | 260/309.5 |
| 3,966,683 | 6/1976 | Merten et al. | 260/309.5 |

OTHER PUBLICATIONS

International Union of Pure and Applied Chemistry, Nomenclature of Organic Chemistry, p. 19, London, Butterworths, 1958.

*Primary Examiner*—Natalie Trousof
*Attorney, Agent, or Firm*—Richard P. Plunkett; William W. McDowell, Jr.

[57] ABSTRACT

This invention relates to polyenes containing at least two ethylenically unsaturated bonds per molecule formed by reacting a hydantoin glycol with an ethylenically unsaturated reactant or adduct containing an isocyanate group. On exposure to a free radical generator, e.g. actinic radiation, the polyenes of the instant invention in combination with a polythiol form a solid, insoluble, crosslinked polythioether product.

6 Claims, No Drawings

HYDANTOIN-CONTAINING POLYENE COMPOSITIONS

This application is a continuation-in-part of my copending application having Ser. No. 614,577, filed Sept. 18, 1975, now abandoned which is a division of Ser. No. 461,207, filed Apr. 15, 1974, now U.S. Pat. No. 3,945,982.

BACKGROUND OF THE INVENTION

The invention relates to a polyene composition. More particularly, this invention relates to a hydantoin-containing polyene composition, a method of preparing same, as well as curing the polyene with a polythiol in the presence of a free radical generator to solid, crosslinked solvent-insoluble materials.

It is known that polyenes are curable by polythiols in the presence of free radical generators such as actinic radiation to solid polythioether containing resinous or elastomeric products. See U.S. Pat. No. 3,661,744. The commercially available polythiols, e. g., mercaptocarboxylate esters of polyols used in curing afford cured polythioether products having a low percent elongation on failure. However, there are several end uses wherein a coating must have a relatively high elongation in order to be operable. For example, it is necessary that a coating on a bottle cap have a relatively high elongation since, after it is applied and cured on the metal blank, the blank is subsequently formed by extrusion or otherwise into cap form which necessitates that the coating have sufficient elongation to follow the contours of the thus formed cap without rupture. Additionally, in bottle coating it is necessary that the cured coating have high elongation to prevent glass shattering. Thus, a curable coating having a high elongation after curing is desirous.

In accordance with this invention a curable polymer composition can be prepared from compatible polyene and polythiol components derived from a hydantoin glycol. This polyene and polythiol mixture is a highly reactive composition which is capable of being photocured when exposed to actinic radiation in the presence of a UV sensitizer to insoluble polythioether containing materials which exhibit excellent physical and chemical properties. For example, wire coatings formed from the cured polyene and polythiol composition are capable of withstanding severe temperature environments for extended periods. The subject cured materials resist strongly acid etching solutions or high alkaline conditions. Additionally the cure polythioether product from the polyenes and polythiols herein has remarkable flexibility and high elongation at failure as will be shown in an example hereinafter. The desirable characteristics of the cured materials make the hydantoin glycol derived polyene-polythiol curable composition particularly useful as coatings on wire and formable metals.

Generally speaking, the novel curable composition is comprised of a polyene component containing at least 2 reactive carbon to carbon unsaturated bonds per molecule which is a reaction product of a hydantoin glycol, e. g. N,N'-bis(2-hydroxyethyl) dimethylhydantoin and at least one unsaturated organic compound such as an ene-isocyanate; and a polythiol component containing at least two thiol groups, which is the reaction product of a hydantoin glycol, e. g. N,N'-bis(2-hydroxyethyl) dimethylhydantoin and a mercaptocarboxylic acid.

The polyene has the general formula:

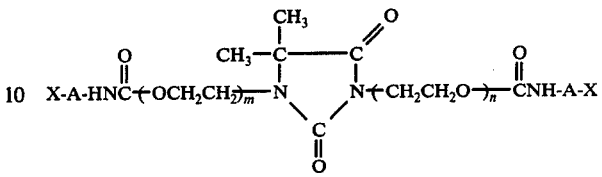

wherein

A is a member of the group consisting of alkylene having from 1 to about 10 carbon atoms, cycloalkylene having from 5 to 15 carbon atoms, arylene, alkarylene and aralkylene each having from 6 to about 13 carbon atoms;

X is a member of the group consisting of

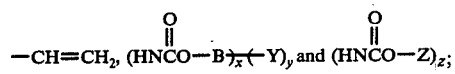

B is alkylene having from 1 to 36 carbon atoms;
Y is a member of the group consisting of

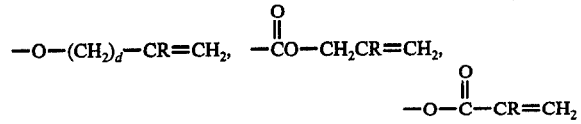

and mixtures thereof with the proviso that no more than one Y can be on one carbon atom of B;

Z is $-(CH_2)_d-CR=CH_2$;

R is hydrogen or methyl; $x$ is 1 to 3; $y$ and $d$ are 1 to 10 with the proviso that the combination of $x$ and $y$ are within conventional combinations; $z$ is 1 to 3; $m$ and $n$ are each integers of at least 1 with $m + n$ in the range 2 to 22.

Operable hydantoin glycols used herein to form either the polyene or the polythiol are those of the formula:

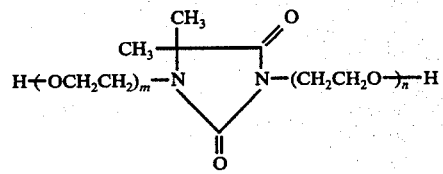

wherein $m + n$ are 2 to 22 and $m$ and $n$ are each at least 1. These hydantoin glycols are commercially available.

The formation of such polyenes may be schematically represented by the following nonlimiting equation, wherein the unsaturated organic compound reactant is an ene-isocyanate having reactive allylic end groups as illustrated by a reaction product of one mole of 2,4-toluene diisocyanate with one mole of allyl alcohol:

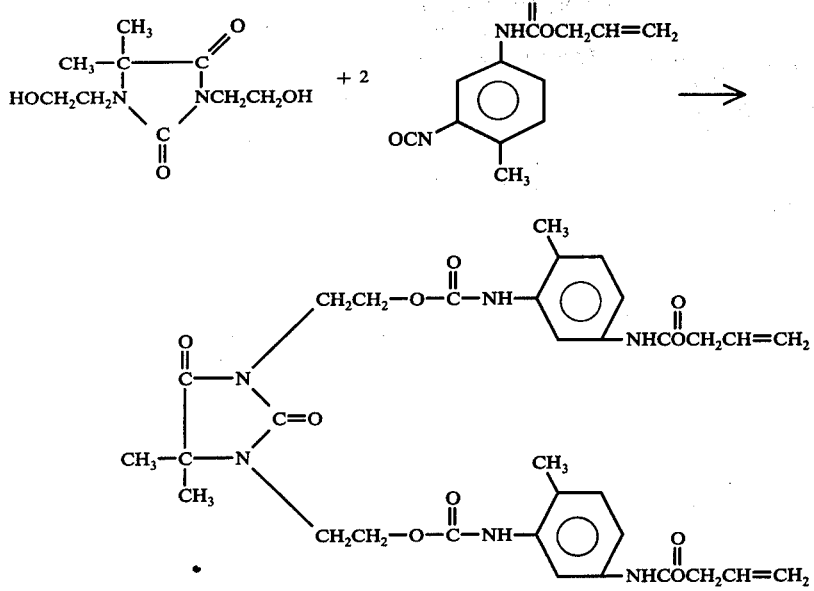

Similarly, the formation of the polythiol may be represented by the nonlimiting equation illustrating β-mercaptopropionic acid as the mercaptocarboxylic reactant:

II.

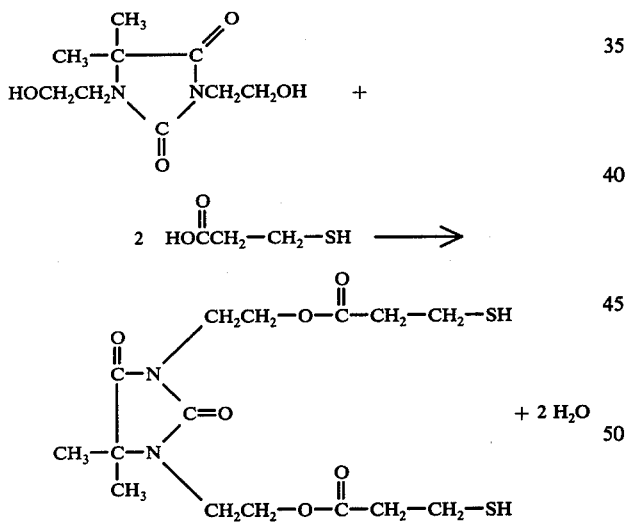

Furthermore, the hydantoin glycols are commercially available materials. The operable hydantoin glycols include not only N,N'-bis(2-hydroxyethyl) dimethylhydantoin, but also polyethoxylated derivatives thereof. These polyethoxylated derivatives are formed by the addition of the desired number of moles of ethylene oxide to the N,N'-bis(2-hydroxyethyl) dimethylhydantoin, i.e., by a conventional epoxide ring-opening addition reaction.

The aforedescribed hydantoin glycols are operable starting materials for the formation of both the polyene and polythiol.

In the curable polyene-polythiol containing compositions, the hydantoin glycols backbone may be either identical or different for both the polyene and polythiol components.

One group of operable polyenes containing hydantoin glycol backbones are unsaturated urethane derivatives. These polyenes, i.e., unsaturated urethane derivatives of hydantoin glycol may be represented by the general formula:

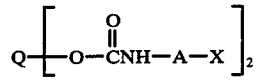

wherein
Q is the hydantoin glycol moiety remaining after the two hydroxyl groups of the hydantoin glycol have reacted to form two urethane, i. e.

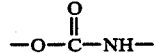

linkages;
A is a member of the group consisting of alkylene having from 1 to about 10 carbon atoms, cycloalkylene having from 5 to 15 carbon atoms, arylene, alkarylene and aralkylene each having from 6 to about 13 carbon atoms;
X is a member of the group consisting of

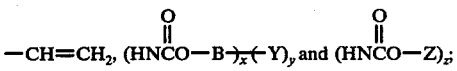

B is alkylene having from 1 to 36 carbon atoms;
Y is a member of the group consisting of

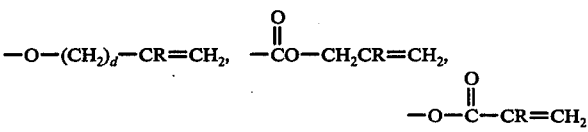

and mixtures thereof;

Z is $-(CH_2)_d-CR=CH_2$;

R is hydrogen or methyl; $x$ is 1 to 3; $y$ and $d$ are 1 to 10; $z$ is 1 to 3.

As used herein, polyenes refer to simple or complex species of alkenes having a multiplicity of pendant or terminally reactive carbon to carbon unsaturated functional groups per average molecule. For example, a diene is a polyene that has two reactive carbon to carbon double bonds per average molecule. For purposes of brevity, all these classes of compounds will be referred to hereafter as polyenes.

In defining the position of the reactive functional carbon to carbon unsaturation, the term terminal is intended to mean that functional unsaturation is at an end of the main chain in the molecule. The term pendant means that the reactive carbon to carbon unsaturation is located terminal in a branch of the main chain as contrasted to a position at or near the ends of the main chain. For purposes of brevity, all of these positions are referred to herein generally as terminal unsaturation.

Functionality as used herein refers to the average number of ene or thiol groups per molecule in the polyene or polythiol, respectively. For example, a triene is a polyene with an average of three reactive carbon to carbon unsaturated groups per molecule, and thus has a functionality (f) of three. A dithiol is a polythiol with an average of two thiol groups per molecule and thus has a functionality (f) of two.

The term reactive unsaturated carbon to carbon groups means groups which will react under proper conditions as set forth herein with thiol groups to yield the thioether linkage

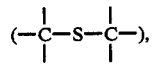

as contrasted to the term unreactive carbon to carbon unsaturation which means

groups found in aromatic nuclei (cyclic structures exemplified by benzene, pyridine, anthracene, and the like) which do not under the same conditions react with thiols to give thioether linkages. For purposes of brevity, this term will hereinafter be referred to generally as reactive unsaturation or a reactive unsaturated compound.

As used herein, the term polyvalent means having a valence of two or greater.

A general method of forming the urethane-containing hydantoin glycol based polyene is to react the hydantoin glycol material represented by a general formula:

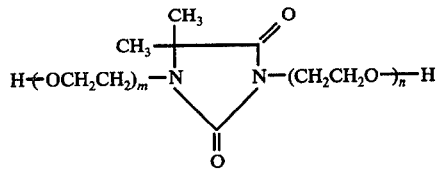

wherein $m + n$ are 2 to 22 and $m$ and $n$ are each at least 1, with at least one reactive ethylenically unsaturated isocyanate of the general formula OCN—A—X in which the members A and X are as hereinbefore set forth.

The term reactive unsaturated isocyanate will hereinafter be referred to as an ene-isocyanate adduct or reactant.

When the ene-isocyanate is a reactant, i.e. a commercially available ethylenically unsaturared isocyanate, such as allylisocyanate, only a one-step reaction is required to form the polyene. In the case where the eneisocyanate is an adduct, a two-step reaction is preferably employed. That is, in the first step the ene-isocyanate adduct is formed by the conventional urethane forming reaction between a polyisocyanate and a reactive ethylenically unsaturated alcohol. The adduct-forming reaction is carried out in a moisture-free atmosphere at atmospheric pressure at a temperature in the range of from about 30°–100° C, preferably from about 40°–80° C for a period of about 10 minutes to about 24 hours. The ethylenically unsaturated alcohol is added in an amount necessary to react with all but one of the isocyanate groups on the polyisocyanate to form urethane linkages. The reaction, if desired, may be carried out in the presence of a catalyst and an inert solvent. Operable non-limiting catalysts include tin catalysts such as dibutyl tin dilaurate, stannous octoate; tertiary amines such as triethylene diamine or N,N,N',N'-tetramethyl-1,3-butanediamine, etc. Useful inert solvents include aromatic hydrocarbons and mixtures thereof. Representative non-limiting examples include benzene, chlorobenzene, chloroform, 1,1,1-trichloroethane, 1,2-dichloroethane and the like.

The ene-isocyanate adduct or reactant is reacted with the hydantoin glycol material in a moisture-free atmosphere at atmospheric pressure at a temperature in the range from about 30°–100° C, preferably from about 40°–80° C for a period of about 10 minutes to about 24 hours. The ene-isocyanate adduct or reactant is added in a stoichiometric amount necessary for the remaining isocyanate groups to react with the hydroxyl groups in the hydantoin glycol. The reaction, if desired, may be carried out in the presence of a catalyst and inert solvent. Operable non-limiting catalysts include thin catalysts such as dibutyl tin dilaurate, stannous octoate; tertiary amines such as triethylene diamine or N,N,N',N'-tetramethyl-1,3-butanediamine, etc. Useful non-limiting inert solvents include aromatic hydrocarbons, halogenated saturated aliphatic or aromatic hydrocarbons and mixtures thereof. Representative non-limiting examples include benzene, chlorobenzene, chloroform, 1,1,1-trichloroethane, 1,2-dichloroethane and the like.

Operable ene-isocyanate rectants include, but are not limited to, simple, commercially available mono-eneisocyanates such as allyl isocyanate, 2-methallyl isocyanate, crotyl isocyanate, and the like.

Operable non-limiting examples of starting polyisocyanates to form the ene-isocyanate adducts and reactants include, but are not limited to, methylenebis(phenyl isocyanate), 2,7-di(isocyanato)-heptane, 1-methoxy-2,4,6-benzenetrisocyanate, 2,4,4'-triisocyanatodiphenylether, diphenylmethane tetraisocyanate, 3,5,5-trimethyl-1-isocyanato-methylcyclohexane, 1,5-naphthylene diisocyanate, 4,4'-diisocyanate diphenyl ether, 2,4-tolylene diisocyanate, 2,6-tolylene diisocyanate, 4,4'-diphenylmethane diisocyanate, dianisidine diisocyanate, tolidine diisocyanate, hexamethylene diisocyanate, the m- and p-xylylene diisocyanates, tetramethylene diisocyanate, 4,4'-methylene bis(cyclohexyl) isocyanate), cyclohexane-1,4-diisocyanate diphenyl ether, 2,4,6-triisocyanate toluene, 4,4',4''-triisocyanate triphenyl methane, diphenylene-4,4-diisocyanate, 1,5-naphthalene diisocyanate, cumene-2,4-diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene diisocyanate, 2,4'-diisocyanato diphenyl ether, 4,5-dimethyl-1,3-phenylene diisocyanate, 2,4-dimethyl-1,3-phenylene diisocyanate, 4,4'-diisocyanato diphenyl ether, benzidine diisocyanate, 4,6-dimethyl-1,3-phenylene diisocyanate, 9,10-anthracene diisocyanate, 4,4'-diisocyanato dibenzyl, 3,3'-dimethyl-4,4''-diisocyanato diphenyl, 2,4-diisocyanatostilbene, 3,3'-dimethyl-4,4''-diisocyanato phenyl methane, 3,3'-dimethoxy-4,4''-diisocyanato diphenyl, 1,4-anthracene diisocyanate, 2,5-fluorene diisocyanate, 1,8-naphthalene diisocyanate, 2,6-diisocyanato benzfuran, amyl benzene-2,4-diisocyanate, hexyl benzene-2,4-diisocyanate, dodecyl benzene-2,4-diisocyanate, butyl benzene-2,4-diisocyanate, polymethylene diisocyanates, such as tretramethylene diisocyanate pentamethylene diisocyanate hexamethylene diisocyanate, cycloalkylene diisocyanates, such as cyclohexylene-1,4-diisocyanate, adducts of polyalcohols and diisocyanates which have at least 2 free isocyanate groups, e.g. adducts of trimethyolpropane and 3 moles of toluene diisocyanate, and the like. Additionally, polyisocyanates having various functional groups such as N,N,N'''-tris(isocyanatohexyl)-biuret are operable.

Illustrative of the operable reactive unsaturated alcohols which react with the polyisocyanates to give the desired ene-isocyanate include, but are not limited to, allyl and methallyl alcohol, crotyl alcohol, ω-undecylenyl alcohol, 2-vinyloxyethanol, vinylhydroxyethyl sulfide, propargyl alcohol, hydroxy ethuyl acrylate, hydroxy ethyl methacrylate, 1-allylcyclopentanol, 2-methyl-3-butene-2-ol, diallyl malate, hydroxy propyl acrylate, hydroxy propyl methacrylate. Reactive unsaturated derivatives of polyhydric alcohols such as glycols, triols, tetraols, etc., are also suitable. Representative examples include trimethylolpropane or trimethylolethane diallyl ethers, pentarythritol triallyl ether and the like. Mixtures of various reactive unsaturated alcohols are operable as well. A suitable ene-isocyanate is prepared by treating one mole of trimethylbenzene triisocyanate with two moles of trimethylolpropane diallyl ether. The resulting urethane containing ene-isocyanate is a polyene having four reactive allyl ether groups per molecule. Mixtures of various ene-isocyanates are operable as well.

Following the general procedure set out supra and using the necessary reactive components, adducts and reactants of the following structures are formed resulting in the following A and X groups from the general polyene formula:

| Example No. | Adduct Components | Adduct Formed | Portion of Polyene General Formula — A | Portion of Polyene General Formula — X |
|---|---|---|---|---|
| 1 | Isophorone diisocyanate; Allyl alcohol | (cyclohexyl ring with CH₃, CH₃, CH₂—, CH₃ substituents; OCN and CH₂NHCOCH₂CH=CH₂) | (trimethyl-substituted cyclohexyl with CH₂—) | —NHCOCH₂CH=CH₂ |
| 2 | Toluene diisocyanate; Hydroxy propyl acrylate | methyl-phenyl with NHCOCH—CH₂—OCCH=CH₂ (CH₃); NCO | methyl-phenyl | —NHCOCH—CH₂—OCCH=CH₂ (CH₃) |
| 3 | 1,5-naphthalene diisocyanate; Trimethylol propane diallyl ether | naphthyl with NHCOCH₂—C(CH₂CH₃)(CH₂OCH₂CH=CH₂)₂; NCO | naphthyl | —NHCOCH₂—C(CH₂CH₃)(CH₂OCH₂CH=CH₂)(CH₂OCH₂CH=CH₂) |
| 4 | 4,4′-methylene bis(cyclohexyl); Allyl alcohol | OCN—cyclohexyl—CH₂—cyclohexyl—NHCOCH₂CH=CH₂ | cyclohexyl—CH₂—cyclohexyl | —NHCOCH₂CH=CH₂ |
| 5 | Hexamethylene diisocyanate; Diallyl malate | OCN(CH₂)₆NHCO—CH(OCCH₂CH=CH₂)—CH₂—(OCCH₂CH=CH₂) | —(CH₂)₆— | —NHCO—CH(OCCH₂CH=CH₂)—CH₂—(OCCH₂CH=CH₂) |
| 6 | 2,4,6-triisocyanate toluene; Trimethylol propane diallyl ether | trimethyl-phenyl (CH₃) with two NHCOCH₂—C(CH₂CH₃)(CH₂OCH₂CH=CH₂)₂ groups and OCN | methyl-phenyl | {—NHCOCH₂—C(CH₂CH₃)(CH₂OCH₂CH=CH₂)(CH₂OCH₂CH=CH₂)}₂ |

-continued

| Example No. | Adduct Components | Adduct Formed | Portion of Polyene General Formula A | Portion of Polyene General Formula X |
|---|---|---|---|---|
| 7 | 2,4,6-triisocyanate toluene; Pentaerythritol triacrylate | (structure: toluene ring with CH₃, OCN, and two NHCOCH₂—C(CH₂OCCH=CH₂)₂—CH₂OCCH=CH₂ groups) | (toluene ring with CH₃) | $-\text{NHCOCH}_2-\underset{\underset{\text{CH}_2\text{OCCH=CH}_2}{\mid}}{\overset{\overset{\text{CH}_2\text{OCCH=CH}_2}{\mid}}{\text{C}}}-\text{CH}_2\text{OCCH=CH}_2$ (taken twice) |
| 8 | Xylylene diisocyanate; Allyl alcohol | OCNCH₂—(phenyl)—CH₂NHCOCH₂CH=CH₂ | —CH₂—(phenyl)—CH₂— | —NHCOCH₂CH=CH₂ |
| 9 | Allyl isocyanate | OCN—CH₂CH=CH₂ | —CH₂— | —CH=CH₂ |

The polythiol component of the curable composition is mercaptoester having two thiol groups per molecule. The polythiol is a reaction product of hydantoin glycol and at least one mercaptocarboxylic acid. The polythiols may be represented by the following general formula:

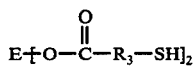

and E is the hydantoin glycol moiety remaining after removal of the 2 hydroxyl groups from the hydantoin glycol thereby forming 2 ester linkages; $R_3$ is a polyvalent organic radical member free of reactive carbon to carbon unsaturation and contains group members such as aryl, substituted aryl, aralkyl, substituted aralkyl, cycloalkyl, substituted cycloalkyl, akyl and substituted alkyl groups containing 1 to 16 carbon atoms.

Preferred examples of operable aryl members are either phenyl or naphthyl, and of operable cycloalkyl members which have from 3 to 8 carbon atoms. Likewise, preferred substituents on the substituted members may be such groups as chloro, bromo, nitro, acetoxy, acetamido, phenyl, benzyl, alkyl and alkoxy of 1 to 9 carbon atoms, and cycloalkyl of 3 to 8 carbon atoms.

Operable hydantoin glycols used herein to form the polythiol are those of the formula:

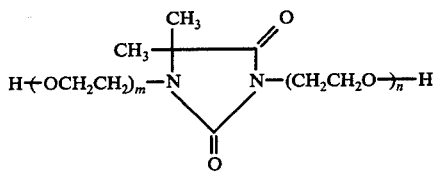

wherein $m + n$ are 2 to 22 and $m$ and $n$ are each at least 1.

Operable mercaptocarboxylic acids include but are not limited to thioglycollic acid (mercaptoacetic acid), α-mercaptopropionic acid, β-mercaptopropionic acid, 4-mercaptobutyric acid, mercaptovaleric acids, mercaptoundecylic acid, mercaptostearic acid, and o- and p-mercaptobenzoic acids. Preferably, thioglycollic or β-mercaptopropionic acid is employed. Mixtures of various mercaptocarboxylic acids are operable as well.

The polythiol esters are prepared by the esterfication of the hydantoin glycol with mercaptocarboxylic acid in the presence of an acid catalyst, the water formed during the reaction being removed as an azeotrope in a suitable solvent.

The reaction is carried out at atmospheric pressure at a temperature in the range of from 60° to about 150° C, preferably from 60° to 110° C. for a period of 30 minutes to about 24 hours.

Suitable acid catalysts include but are not limited to p-toluenesulfonic acid, sulfuric acid, hydrochloric acid and the like. Useful inert solvents include but are not limited to saturated aliphatic hydrocarbons, aromatic hydrocarbons, chlorinated hydrocarbons, ethers, ketones, etc. Representative non-limiting examples of solvents include toluene, benzene, xylene, chloroform, 1,2-dichloroethane, etc.

In summary, by admixing the novel hydantoin glycol based polyenes and polythiols and thereafter exposing the mixture at ambient conditions to a free radical generator, a solid, cured insoluble polythioether product having a high percent elongation is obtained.

Prior to curing, the polyene and polythiol components are admixed in a suitable manner so as to form a homogeneous curable mixture. Thus, the polyene and polythiol reactants can be admixed without the necessity of using a solvent at room temperature or slightly elevated temperature up to about 80° C or, if desired, the reactants may be dissolved in a suitable solvent and, thereafter, the solvent can be removed by suitable means such as evaporation.

To obtain the maximum strength, solvent resistance, creep resistance, heat resistance and freedom from tackiness, the reactive components consisting of the polyenes and polythiols are formulated in such a manner as to give solid, crosslinked, three dimensional network polythioether polymer systems on curing. In order to achieve such infinite network formation, the individual polyenes and polythiols must each have a functionality of at least 2 and the sum of the functionalities of the polyene and polythiol components must always be greater than 4. Blends and mixtures of various polyenes and various polythiols containing said functionality are also operable herein.

The compositions to be cured in accord with the present invention may, if desired, include such additives as antioxidants, accelerators, dyes, inhibitors, activators, fillers, thickeners, pigments, anti-static agents, flame-retardant agenrts, surface-active agents, extending oils, plasticizers, thioxotropic agents and the like within the scope of this invention. Such additives are usually pre-blended with the polyene or polythiol prior to or during the compounding step. The aforesaid additives may be present in quantities up to 500 or more parts based on 100 parts by weight of the polyene-polythiol curable compositions and preferably 0.005–300 parts on the same basis.

The polythioether-forming components and compositions, prior to curing, may be admixed with or blended with reactive diluents, other monomeric and polymeric materials such as thermoplastic resins, elastomers or thermosetting resin monomeric or polymeric compositions.

Non-limiting reactive diluents operable herein include ethylene glycol diacrylate, ethylene glycol dimethacrylate, diethylene glycol diacrylate, diethylene glycol dimethacrylate, trimethylol propane triacrylate, trimethylol propane trimethacrylate, pentaerythritol tetracrylate, pentaerythritol tetramethacrylate, 1,6-hexanediol diacrylate, 1,6-hexanediol dimethacrylate, pentaerythritol triacrylate, neopentyl glycol diacrylate and mixtures thereof. The resulting blend may be subjected to conditions for curing or co-curing of the various components of the blend to give cured products having unusual physical properties.

Although the mechanism of the curing reaction is not completely understood, it appears most likely that the curing reaction may be initiated by most any free radical generating source which dissociates or abstracts a hydrogen atom from an SH group, or accomplishes the equivalent thereof. Generally, the rate of the curing reaction may be increased by increasing the temperature of the composition at the time of initiation of cure. In most applications, however, the curing is accomplished conveniently and economically by operating at ordinary room temperature conditions.

Operable curing initiators or accelerators include radiation such as actinic radiation, e.g., ultraviolet light, lasers; ionizing radiation such as gamma radiation, x-rays, corona discharge, etc.; as well as chemical free radical generating compounds such as azo, peroxidic, etc., compounds.

Azo or peroxidic compounds (with or without amine accelerators) which decompose at ambient conditions are operable as free radical generating agents capable of accelerating the curing reaction include benzoyl peroxide, di-t-butyl peroxide, cyclohexanone peroxide with dimethyl aniline or cobalt naphthenate as an accelerator; hydroperoxides such as hydrogen peroxide, cumene hydroperoxide, t-butyl hydroperoxides; peracid compounds such as t-butylperbenzoate, peracetic acid; persulfates, e.g., ammonium persulfate; azo compounds such as azobis-isobutyronitrile and the like.

These free radical generating agents are usually added in amounts ranging from about 0.001 to 10 percent by weight of the curable solid polyene-polythiol composition, preferably .01 to 5 percent.

The curing period may be retarded or accelerated from less than 1 minute to 30 days or more.

Conventional curing inhibitors or retarders which may be used in order to stabilize the components or curable compositions so as to prevent premature onset of curing may include hydroquinone; p-tert-butyl catechol; 2,6-di tert-butyl-p-methylphenol; phenothiazine; N-phenyl-2-naphthylamine; phosphorous acid; pyrogallol and the like.

The preferred free radical generator for the curing reaction is actinic radiation, suitably in the wavelength of about 2000 to 7500A, preferably for 2000 to 4000A.

A class of actinic light useful herein is ultraviolet light, and other forms of actinic radiation which are normally found in radiation emitted from the sun or from artificial sources such as Type RS Sunlamps, carbon arc lamps, xenon arc lamps, mercury vapor lamps, tungsten halide lamps and the like. Ultraviolet radiation may be used most efficiently if the photocurable polyene/polythiol composition contains a suitable photocuring rate accelerator. Curing periods may be adjusted to be very short and hence commercially economical by proper choice of ultraviolet source, photocuring rate acclelerator and concentration thereof, temperature and molecular weight, and reactive group functionality of the polyene and polythiol. Curing periods of less than about 1 second duration are possible, especially in thin film applications such as desired, for example, in coatings, adhesives and photoimaged surfaces.

Various photosensitizers, i.e., photocuring rate accelerators are operable and well known to those skilled in the art. Examples of photosensitizers include, but are not limited to, benzophenone o-methoxybenzophenone, acetophenone, o-methoxyacetophenone, acenophthenequinone, methyl ethyl ketone, valerophenone, hexanophenone, α-phenylbutyrophenone, p-morpholinopropiophenone, dibenzosuberone, 4-morpholinobenzophenone, benzoin, benzoin methyl ether, 40'-morpholinodeoxybenzoin, p-diacetylbenzene, 4-aminobenzophenone, 4'-methoxyacetopheneone, benzaldehyde, o-methoxybenzaldehyde, α-tetralone, 9-acetylphenanthrene, 2-acetylphenanthrene, 10-thioxanthenone, 3-acetylphenanthrene, 3-acetylindole, 9-fluoroenone, 1-indanone, 1,3,5-triacetylbenzene, thioxanthen-9-one, xanthene-9-one, 7-H-benz[de]anthracen-7-one, 1-naphthaldehyde, benzoin tetrahydropyranyl ether, 4,4'-bis(dimethylamino)benzophenone, fluroene-9-one, 1'-acetonaphthone, 2'-acetonaphthone, triphenylphosphine, tri-o-tolylphosphine, acetonaphthone and 2,3-butanedione, benz[a]anthracene 7,12 dione, 2,2-dimethoxy-2-phenylacetone, diethoxyacetophenone, dubutoxyacetophenone, etc., which serve to give greatly reduced exposure times and thereby, when used in conjunction with various forms of energetic radiation, yield very rapid, commercially practical time cycles by the practice of the instant invention.

These photocuring rate accelerators may range from about 0.005 to 50 percent by weight of the photocurable polyene-polythiol composition, preferably 0.05 to 25 percent.

The mole ratio of the ene/thiol groups for preparing the curable composition is from about 0.2/1.0 to about 8/1.0, and preferably from 0.5/1.0 to about 2/1.0 group ratio.

The curable hydantoin glycol derived polyene and polythiol compositions are used in preparing solid, cured crosslinked insoluble polythioether polymeric products having many and varied uses, examples of which include, but are not limited to, coatings; adhesives; films; molded articles; imaged surfaces, e.g. photoresists; printing plates; e.g. offset, lithographic, letterpress, gravures, etc., silver-less photographic materials and the like.

Since the cured materials formed from the polyene-polythiol composition possess various desirable properties such as resistance to severe chemical and physical environments and have a high percent elongation, they are particularly useful for preparing coatings.

A general method for preparing coatings, comprises coating the curable composition on a solid surface of a substrate such as plastic, rubber, glass, ceramic, metal, paper and the like; exposing directly to radiation, e.g., U.V. light until the curable composition cures and cross-links in the exposed areas. The resulting products are cured coatings on suitable substrates or supports.

In forming the composition comprised of the polythiol and the polyene, it is desirable that the photocurable composition contain a photocuring rate accelerator from about 0.005 to 50 parts by weight based on 100 parts by weight of the aforementioned polyene and polythiol.

It is to be understood, however, that when energy sources, e.g., ionizing radiation, other than visible or ultraviolet light, are used to initiate the curing reaction, photocuring rate accelerators (i.e., photosensitizers, etc.) generally are not required in the formulation.

When U. V. radiation is used for the curing reaction, a dose of 0.0004 to 6.0 watts/cm$^2$ is usually employed.

The following examples will aid in explaining, but should not be deemed limiting, the instant invention. In all cases unless otherwise noted, all parts and percentages are by weight.

EXAMPLE I

To a 3,000 ml. resin kettle equipped with stirrer, thermometer, nitrogen inlet and outlet and vented addition funnel was charged under a nitrogen blanket 959.4 grams of commercially available trimethylolpropane diallyl ether and 0.98 grams of stannous octoate catalyst. 1,000 grams of commercially available isophorone diisocyanate was charged to the addition funnel and added dropwise to the kettle with stirring over a 4 ½ hour period while maintaining the temperature below 70° C. After the isophorone diisocyanate was completely added, the temperature was allowed to drop to room temperature (24° C), the nitrogen blanket discontinued and the reaction was stirred for 48 hours.

To a separate 1,000 ml. resin kettle equipped with stirrer, thermometer, nitrogen inlet and outlet and vented addition funnel was charged 535 grams of the reaction product from above along with 16 drops of stannous octoate. 301.3 grams of commercially available pentaethoxylated N,N'-bis(2-hydroxyethyl) dimethylhydantoin was charged to the addition funnel and thereafter added dropwise to the resin kettle with stirring while maintaining the temperature below 70° C. The resultant polyene product of the formula:

leum ether was added to precipitate the product as a fine white powder. The powder was filtered and dried in vacuo. It contained a carbon-to-carbon unsaturation of 2.7 mmoles/g. This resulting polyene has the formula:

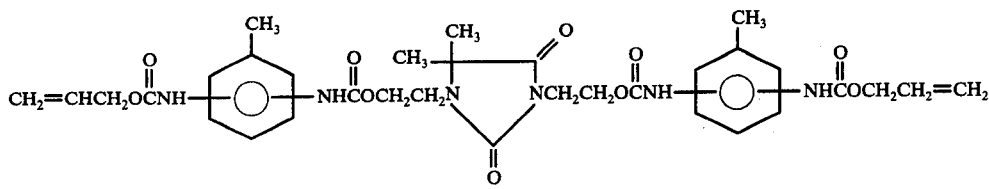

This polyene will hereinafter be referred to as Polyene B.

EXAMPLE III

To a 1,000 ml. resin kettle equipped with stirrer, ther-

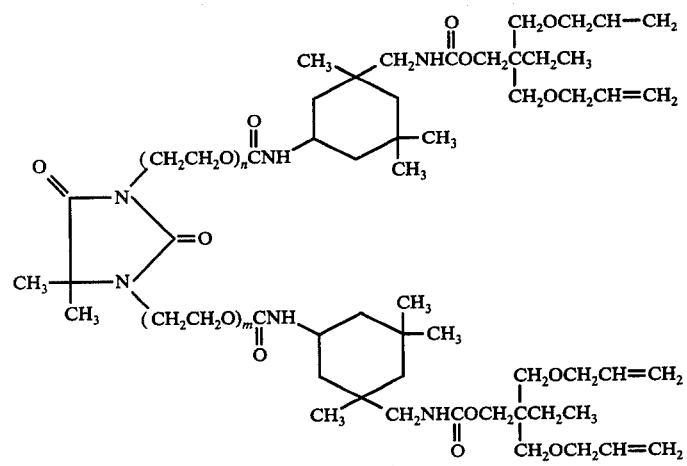

wherein m + n equals 7, had a carbon to carbon unsaturation content of 2.9 mmoles/g.

This polyene will be referred to hereinafter as Polyene A.

EXAMPLE II

To a 3,000 ml. resin kettle equipped with stirrer, thermometer, nitrogen inlet and outlet and vented addition funnel was charged under a nitrogen blanket 261 grams of commercially available tolylene diisocyanate. 87 grams of commercially available allyl alchol was added to the addition funnel and thereafter added dropwise to the resin kettle with stirring while maintaining the temperature below 85° C. After 1 ½ hours the addition was complete and the reaction was stirred for an additional 1 ½ hours at which time the isocyanate was analyzed and was found to be 4.26 meq./g.

325 grams of the reaction product was transferred to a 200 ml. resin kettle similarly equipped as above and containing 400 ml. chloroform and 0.25 gram stannous octoate. 151.3 grams of commercially available N,N'-bis(2-hydroxyethyl) dimethylhydantoin was added to the resin kettle and a definite exotherm was noted. The NCO band in the IR was followed until disappearance. The material was transferred to a blender and petromometer, nitrogen inlet and outlet and vented addition funnel was charged 294.8 grams of commercially available tolylene diisocyanate. 365.2 grams of trimethylolpropane diallyl ether was charged to the addition funnel and thereafter added dropwise to the resin kettle under a nitrogen atmosphere while maintaining the temperature below 28° C. After the addition was complete the material was stirred for about 4 hours. The material had a NCO content of 2.47 meq./g.

To another 1,000 ml. resin kettle equipped with stirrer, thermometer, nitrogen inlet and outlet and an addition funnel as charged 200 grams of commercially available pentadecaethoxylated N,N'-bis(2-hydroxyethyl) dimethylhydantoin having an OH content of 1.95 meq./g. along with 3 drops of stannous octoate. 157.2 grams of the reaction product of the tolylene diisocyanate and the trimethylolpropane diallyl ether reaction supra was charged to the addition funnel and thereafter added dropwise to the resin kettle. The temperature was maintained below 58° C. during the 4 ½ hours of addition. The reaction was stirred for an additional 21 hours during which time the NCO content was monitored by IR scans. The resultant polyene had a carbon to carbon unsaturation of 2.35 mmoles/g. and had the formula:

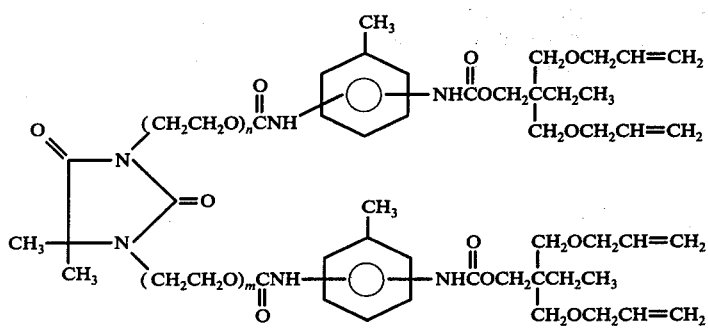

wherein $m + n$ is 17.

This polyene will hereinafter be referred to as Polyene C.

EXAMPLE IV

Example III was repeated except that 226 grams of the reaction product of tolylene diisocyanate and trimethylolpropane diallyl ether was added to 200 grams of commercially available decaethoxylated N,N'-bis(2-hydroxyethyl)dimethylhydantoin. The resultant polyene had a C═C content of 2.72 meq./g. and had the formula:

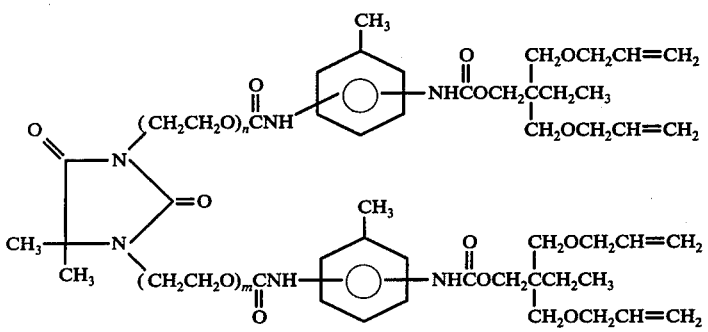

wherein $m + n$ is 12.

This polyene will hereinafter be referred to as Polyene D.

EXAMPLE V

Example III was repeated except that 326 grams of the reaction product of tolylene diisocyanate and trimethylolpropane diallyl ether was added to 200 grams of commercially available pentaethoxylated N,N'-bis(2-hydroxyethyl) dimethylhydantoin. The resultant polyene had a carbon to carbon unsaturation of 3.17 mmoles/g. and had the formula:

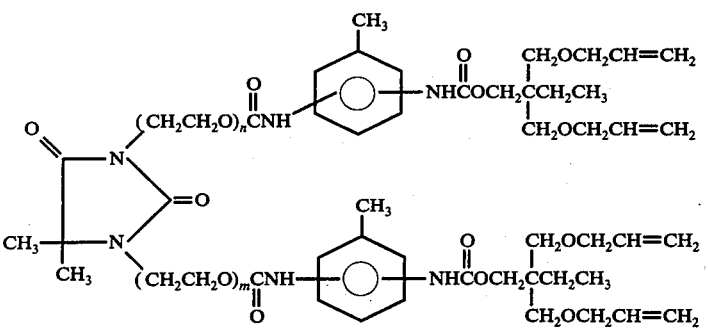

wherein $m + n$ is 7.

This polyene will hereinafter be referred to as Polyene E.

EXAMPLE VI

To a 3,000 ml. resin kettle equipped with stirrer thermometer, nitrogen inlet and outlet and addition funnel was charged under a nitrogen blanket 250 grams of commercially available tolylene diisocyanate along with 0.28 grams of stannous octoate catalyst. 323.14 grams of diallyl malate was charged to the addition funnel and thereafter added dropwise to the resin kettle with stirring while maintaining the temperature below 58° C. The reaction was continued for 4 hours. 529 grams of the reaction product was transferred to a dropping funnel and thereafter added dropwise to a 2,000 ml. resin kettle containing 147.4 grams of commercially available N,N'-bis(2-hydroxyethyl) dimethylhydantoin and 0.39 grams stannous octoate. The reaction thickened as addition continued and the temperature was allowed to rise to about 100° C to permit stripping. An additional 0.39 grams of stannous octoate was added to the reaction and the reaction was continued for 51 hours at which time the IR scan showed zero NCO.

The resultant polyene had a C=C content of 4.06 mmoles/g. and was of the formula:

had a glass melting point of 95° C, unsaturation: theory, 3.66 mmoles/g; found, 3.78 mmoles/g. This polyene

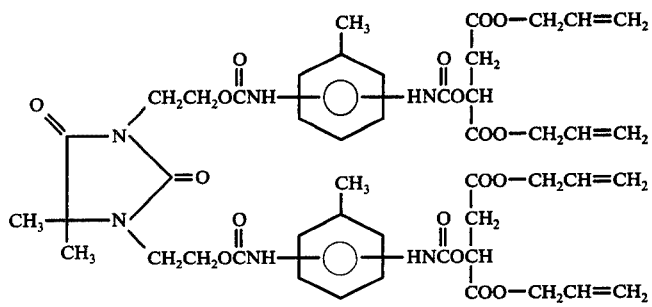

This polyene will hereinaftr be referred to as Polyene F.

EXAMPLE VII

To a 3,000 ml. resin kettle equipped with stirrer, thermometer, nitrogen inlet and outlet and vented addition funnel was charged under a nitrogen blanket 959.4 grams of commercially available trimethylolpropane diallyl ether and 0.98 grams of stannous octoate catalyst. 1,000 grams of commercially available isophorone diisocyanate was charged to the addition funnel and added dropwise to the kettle with stirring over a 4 ½ hour period while maintaining the temperature below 70° C. After the isophorone diisocyanate was completely added, the temperature was allowed to drop to room temperature (24° C), the nitrogen blanket discontinued and the reaction was stirred for 48 hours.

To a separate 1,000 ml. resin kettle equipped with stirrer, thermometer, nitrogen inlet and outlet and vented addition funnel was charged 597 grams of the reaction product from above along with 16 drops of stannous octoate. 138 grams of commercially available N,N'-bis(2-hydroxyethyl) dimethylhydantoin was charged to the addition funnel and, thereafter, added dropwise to the resin kettle with stirring while maintaining the temperature below 70° C. The resultant polyene product of the formula:

prepolymer will hereinafter be referred to as Prepolymer G.

EXAMPLE VIII 253 g of commercially available trimethylol propane diallyl ether (4.54 meq. OH/g) was added dropwise to a 3-necked flask contaning 200 g of toluene diisocyanate (an 80/20 mixture of the 2,4 and 2,6 isomers) (11.48 meq. NCO/g). The reaction was continued with stirring at 60° C for 8 hours. To the reaction product was added 118 g of commercially available di(2-hydroxyethyl)-dimethylhydantoin (8.92 meq. OH/g) of the formula:

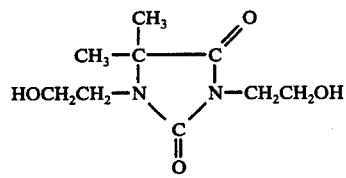

along with 0.25 g of stannous octoate as a catalyst. Some heat was required to start the reaction and, due to the mixture becoming extremely viscous as the reaction proceeds, the temperature had to be raised to 95° C to insure proper mixing. The reaction was maintained at this temperature until complete as shown by the disappearance of the NCO band by IR. The resulting product of the formula:

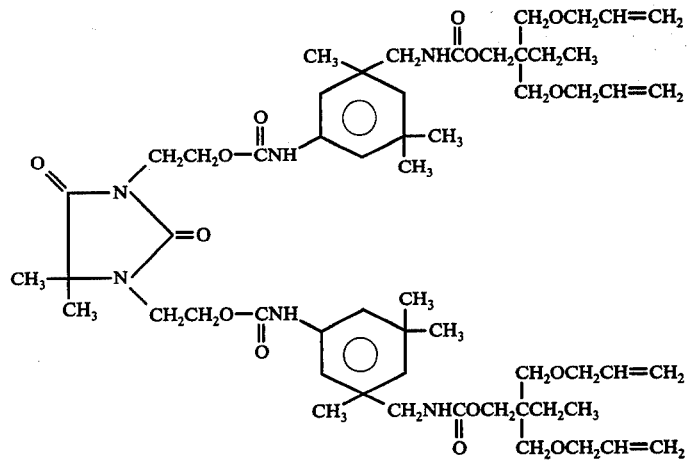

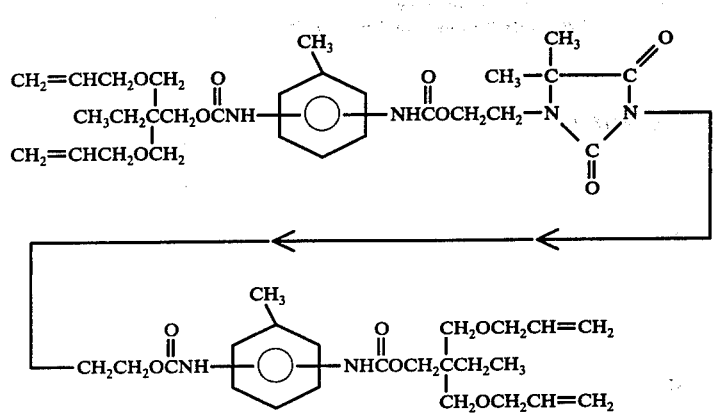

had a class melting point of 95° C, unsaturation: theory, 4.03 mmoles/g; found, 4.06 mmoles/g. This polyene prepolymer will hereinafter be referred to as Prepolymer H.

EXAMPLE IX

To a 1,000 ml. resin kettle equipped with stirrer, thermometer, air inlet and outlet and vented addition funnel was charged under a dry air sparge 250 grams of toluene diisocyanate 0.05 grams of stannous octoate catalyst and 0.31 grams of triphenylphosphite stabilizer. 187 grams of commercially available hydroxypropyl acrylate was charged to the addition funnel and added dropwise to the kettle with stirring over a 4 ½ hour period while maintaining the temperature below 70° C. After the hydroxypropyl acrylate was completely added, the temperature was allowed to drop to room temperature (24° C).

To the product produced above was added dropwise 154 grams of commercially available N,N'-bis(2-hydroxyethyl) dimethylhydantoin. The resltant hydantoin-containing acrylate polyene product was a foamy, hard solid.

EXAMPLE X

To a 2,000 ml. 3-necked flask equipped for distillation with stirrer and nitrogen inlet was charged 432 grams (2 moles) of commercially available N,N'-bis(2-hydroxyethyl) dimethylhydantoin, 445 grams of mercaptopropionic acid and 17.5 grams p-toluenesulfonic acid. 100 ml. of ethylene dichloride was added to the flask. The mixture was heated with stirring for 8 hours and the evolved water was continuously removed by azeotropic distillation at 71°-75° C, returning the ethylene dichloride to the reaction flask. The solution in the flask was then washed once with about 1,000 ml. water, twice with about 1,000 ml. of 5 percent sodium bicarbonate and finally with about 1,000 ml. of water. The solution was dried over anhydrous magnesium sulfate, mixed with 10 g. of decolorizing carbon and filtered. The solvent was removed by vacuum distillation, affording 672 g. of product or an 86 percent yield of the following polythiol:

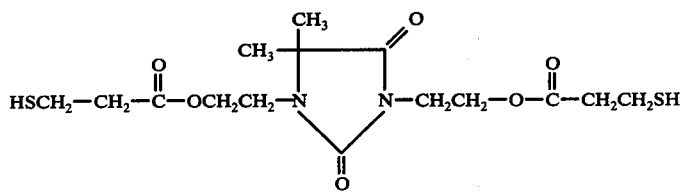

This polythiol will be referred to hereinafter as Polythiol Z.

EXAMPLE XI

To a 2 liter, 3-necked, round-bottom flask equipped with stirrer, thermometer, Dean-Stark trap and reflux condenser was charged 216 grams of commercially available N,N'-bis(2-hydroxyethyl) dimethylhydantoin, 193.2 grams of thioglycollic acid, 8.18 grams of p-toluenesulfonic acid and 500 ml. of benzene. The mixture was heated to reflux temperature with stirring. The amount of water collected in the Dean-Stark trap was periodically determined and the reaction was stopped when 39.5 ml. water was collected. The mixture was cooled to room temperature, washed with 500 ml. water then twice washed with 500 ml. of a 5 percent NaHCO$_3$ solution followed by an additional 500 ml. water wash. The benzene layer was removed and dried over 60 grams anhydrous MgSO$_4$. 2.5 grams decolorizing carbon was then added to the mixture and it was filtered through a fritted filter with the aid of a vacuum. The benzene was stripped off under high vacuum in a flash evaporator to give the polythiol in the amount of 293 grams (80.5 percent yield). On analysis the product had an SH content of 4.96 meq. SH/g., a COOH content of 0.02 meq. COOH/g. and an ester content of 6.07 meq. ester/g. The polythiol had the formula:

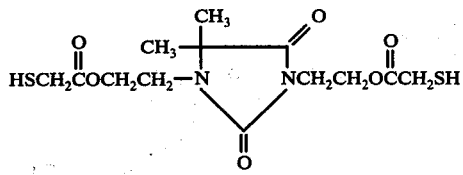

This polythiol will be referred to hereinafter as Polythiol X.

The following examples show the ability of the polyenes and polythiols herein to form cured polythioethers on exposure to actinic radiation. The polyenes and polythiols herein when cured together result in cured materials having a high percent of elongation on failure as compared to other commercially available polyenes and polythiols.

EXAMPLE XII

The following formulations were prepared in 200 ml. brown sample bottles. In all cases accurately weighed amounts of the polyene, stabilizers, photosensitizer and polythiol were added to the bottle and admixed until homogeneous before use. When Polyene A (a solid at room temperature 25° C) was used in the formulation, it was heated to 80° C in order to facilitate weighing and handling.

| Formulation A | |
|---|---|
| Weight (g.) | Component |
| 71.4 | Polyene E |
| 28.6 | pentaerythritol tetrakis (mercaptopropionate) - a polythiol commercially available from Cincinnati Milacron Chemicals, Inc., under the tradename "Q-43" |
| 2.0 | benzophenone (photosensitizer) |
| 0.05 | $H_3PO_3$ (stabilizer) |
| 0.2 | octadecyl-$\beta$-(4-hydroxy-3,5-di-t-butyl phenyl) propionate - commercially available from Geigy-Ciba under the tradename "IRGANOX 1076" (stabilizer) |
| 0.1 | 2,6-di-tert-butyl-4-methyl phenol commercially available under the tradename "Ionol" from Shell Chemical Company (stabilizer) |

| Formulation B | |
|---|---|
| Weight (g.) | Component |
| 72.3 | Polyene E |
| 27.7 | ethylene glycol bis (mercaptopropionate)-a polythiol commercially available under the tradename "E-23" from Cincinnati Milacron Chemicals, Inc. |
| 2.0 | benzophenone |
| 0.05 | $H_3PO_3$ |
| 0.2 | "IRGANOX 1076" |
| 0.1 | "Ionol" |

| Formulation C | |
|---|---|
| Weight (g.) | Component |
| 69.2 | Polyene E |
| 30.8 | trimethylolpropane tris (mercaptopropionate) a polythiol commercially available from Cincinnati Milacron Chemicals, Inc., under the tradename "P-33" |
| 2.0 | benzophenone |
| 0.05 | $H_3PO_3$ |
| 0.2 | "IRGANOX 1076" |
| 0.1 | "Ionol" |

| Formulation D | |
|---|---|
| Weight (g.) | Component |
| 60.75 | Polyene E |
| 39.25 | Polythiol X |
| 2.0 | benzophenone |
| 0.05 | $H_3PO_3$ |
| 0.2 | "IRGANOX 1076" |
| 0.1 | "Ionol" |

| Formulation E | |
|---|---|
| Weight (g.) | Component |
| 79.5 | Polyene A from Example I |
| 30.0 | "Q-43" |
| 2.19 | benzophenone |
| 0.054 | $H_3PO_3$ |
| 0.219 | "IRGANOX 1076" |
| 0.109 | "Ionol" |

| Formulation F | |
|---|---|
| Weight (g.) | Component |
| 65.2 | Polyene A |
| 22.5 | "E-23" |
| 1.95 | benzophenone |
| 0.048 | $H_3PO_3$ |
| 0.195 | "IRGANOX 1076" |
| 0.097 | "Ionol" |

| Formulation G | |
|---|---|
| Weight (g.) | Component |
| 71.3 | Polyene A |
| 30.0 | "P-33" |
| 2.02 | benzophenone |
| 0.050 | $H_3PO_3$ |
| 0.202 | "IRGANOX 1076" |
| 0.101 | "Ionol" |

| Formulation H | |
|---|---|
| Weight (g.) | Component |
| 49.2 | Polyene A |
| 30.0 | Polythiol Z |
| 1.58 | benzophenone |
| 0.039 | $H_3PO_4$ |
| 0.158 | "IRGANOX 1076" |
| 0.079 | "Ionol" |

Each formulation was poured on a glass plate and drawn down to a 20 mil thick film. The film on the plate was exposed to UV radiation for 2 minutes under a UV Ferro lamp at a surface intensity of 7,000 microwatts/cm². The cured samples were measured for percent elongation at failure. The results are shown in Table I.

TABLE I

| Formulation | % Elongation at Failure |
|---|---|
| A | 76 |
| B | 84 |
| C | 66 |
| D | 154 |
| E | 90 |
| F | 75 |
| G | 63 |
| H | 133 |

As can be seen from the results, formulations D and H, consisting of the polyene and polythiol in which both components are derived from a hydantoin glycol, resulted in cured polythioethers having very high percent elongations as compared to the polyenes herein used with commercially available mercaptate esters.

The molecular weight of the polyenes and polythiols of the present invention may be measured by various conventional methods including solution viscosity, osmotic pressure and gel permeation chromatography.

Additionally, the molecular weight may be calculated from the known molecular weight of the reactants.

As can be seen from the above detailed description, the subject curable and particularly photocurable compositions comprised of compatible polyenes and polythiols derived from hydrantoin glycol exhibit extremely satisfactory chemical and physical properties and are versatile curable polyermic systems.

It is understood that the foregoing detailed description is given merely by way of illustration and that many variations may be made therein without departing from the spirit of this invention.

What is claimed is:

1. A polyene of the formula:

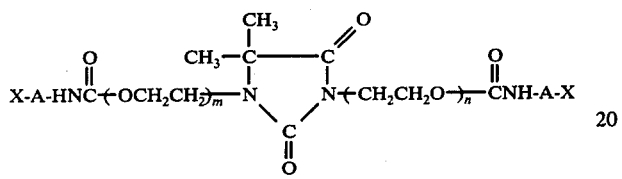

wherein
A is a member of the group consisting of alkylene having from 1 to 10 carbon atoms, cycloalkylene having from 5 to 15 carbon atoms,

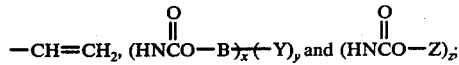

arylene having from 6 to 12 carbon atoms, alkarylene having from 7 to 13 carbon atoms and aralkylene having from 7 to 13 carbon atoms;

X is a member of the group consisting of $$-CH=CH_2, (HNCO-B)_x(-Y)_y, \text{ and } (HNCO-Z)_z;$$

B is alkylene having from 1 to 36 carbon atoms;
Y is a member of the group consisting of

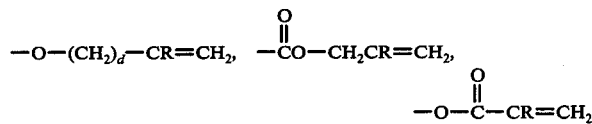

and mixtures thereof with the proviso that no more than one Y can be on one carbon atom of B;

Z is $-(CH_2)_d-CR=CH_2$;

R is hydrogen or methyl; $x$ is 1 to 3; $y$ and $d$ are 1 to 10; $z$ is 1 to 2; $m$ and $n$ are each integers of at least 1 with $m + n$ in the range 2 to 22.

2. A polyene according to claim 1 of the formula:

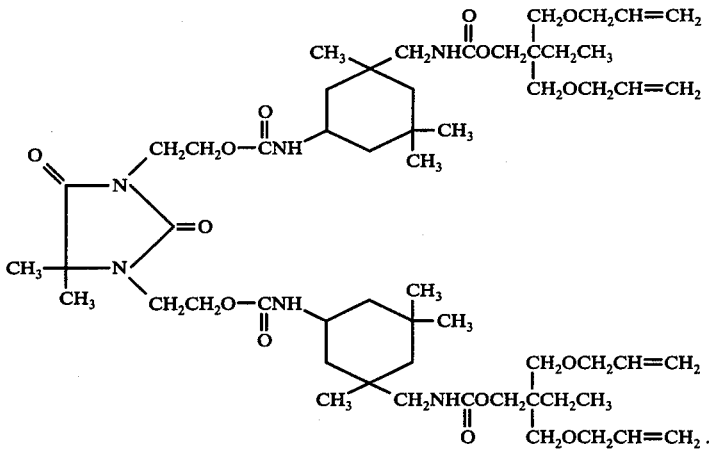

3. A polyene according to claim 1 of the formula:

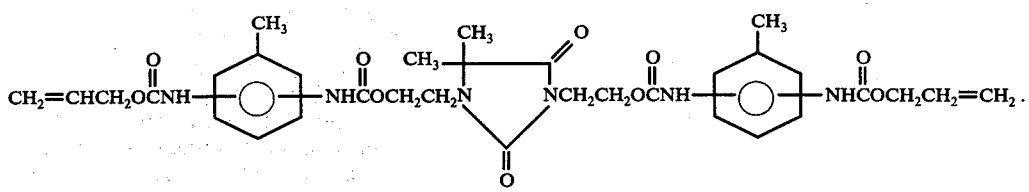

4. A polyene according to claim 1 of the formula:

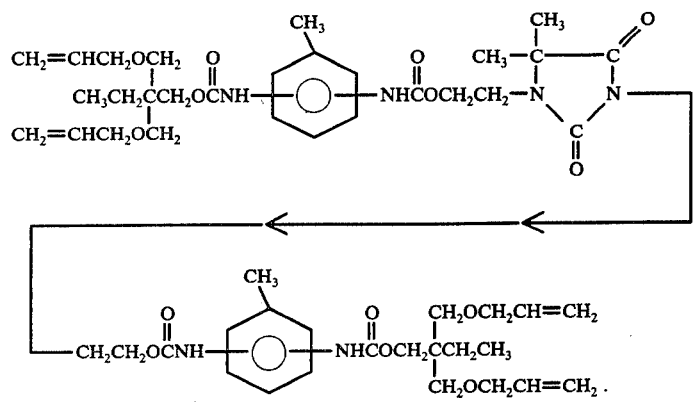
5. A polyene according to claim 1 of the formula: wherein $m + n$ is 7.
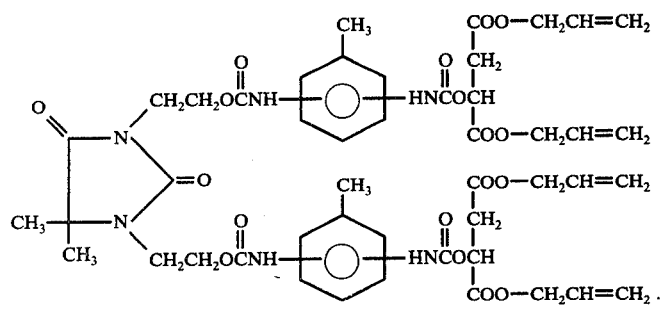
6. A polyene according to claim 1 of the formula:
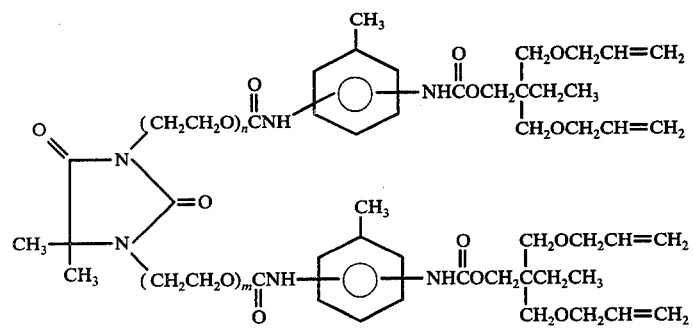
* * * * *